(12) United States Patent
Carpenter et al.

(10) Patent No.: US 8,673,273 B2
(45) Date of Patent: Mar. 18, 2014

(54) HAIR STRAIGHTENING COMPOSITION COMPRISING UREA

(75) Inventors: Paul Carpenter, Wirral (GB); Cheryl Anne Taylor, Wirral (GB); David Tetard, Stanley (GB)

(73) Assignee: Conopco Inc., Englewood Cliffs, NJ (US)

( * ) Notice: Subject to any disclaimer, the term of this patent is extended or adjusted under 35 U.S.C. 154(b) by 561 days.

(21) Appl. No.: 12/086,092

(22) PCT Filed: Nov. 6, 2006

(86) PCT No.: PCT/EP2006/010714
§ 371 (c)(1),
(2), (4) Date: Jun. 5, 2008

(87) PCT Pub. No.: WO2007/065522
PCT Pub. Date: Jun. 14, 2007

(65) Prior Publication Data
US 2009/0252696 A1  Oct. 8, 2009

(30) Foreign Application Priority Data
Dec. 7, 2005  (EP) ..................................... 05257519

(51) Int. Cl.
*A61Q 5/04* (2006.01)
(52) U.S. Cl.
USPC .......................... 424/70.1; 424/401; 424/70.2
(58) Field of Classification Search
USPC ........................................................ 424/70.1
See application file for complete search history.

(56) References Cited

U.S. PATENT DOCUMENTS

| 3,650,280 | A | * | 3/1972 | Roberts et al. | ................ | 132/202 |
| 3,654,936 | A |   | 4/1972 | Wajaroff | ........................... | 132/7 |
| 4,781,724 | A |   | 11/1988 | Wajaroff et al. | .................. | 8/426 |
| 4,793,994 | A | * | 12/1988 | Helioff et al. | ................ | 424/70.4 |
| 4,992,267 | A | * | 2/1991 | DenBeste et al. | .......... | 424/70.51 |
| 5,206,385 | A | * | 4/1993 | Login et al. | .................... | 548/543 |
| 5,338,540 | A | * | 8/1994 | Lee et al. | ..................... | 424/70.4 |
| 7,468,180 | B2 | * | 12/2008 | Van Nguyen et al. | ....... | 424/70.1 |

FOREIGN PATENT DOCUMENTS

| DE | 1 492 078 | 10/1969 |
| DE | 1 955 823 | 3/1971 |
| DE | 35 43 453 | 6/1987 |
| EP | 200 208 | 11/1986 |
| GB | 1 129 527 | 10/1968 |
| JP | 2000 229819 | 8/2000 |
| JP | 2003 212737 | 7/2003 |

OTHER PUBLICATIONS

Urea Material safety data sheet. CF industries. Apr. 2000, 7 pages.*
Wong et al. Mecahnism of hair striagheting. J. Soc Cosmet Chem.4, 5, 347-352 (Nov./Dec. 1994).*
PCT International Search Report in PCT application PCT/EP2006/010714.

* cited by examiner

*Primary Examiner* — Lakshmi Channavajjala
(74) *Attorney, Agent, or Firm* — Ronald A. Koatz

(57) ABSTRACT

An aqueous based hair straightening composition having a pH from 12 to 14 comprising i) an hydroxide ion generator; and ii) from 0.5 wt % to 20 wt % of the total composition of urea in which the weight ratio of urea to hydroxide generator is greater than 1:1.

4 Claims, No Drawings

HAIR STRAIGHTENING COMPOSITION COMPRISING UREA

FIELD OF THE INVENTION

The present invention relates to compositions for straightening hair.

BACKGROUND AND PRIOR ART

Straightening or relaxing the curls of very curly hair is thought to increase the manageability and ease of styling of such hair. There is an increasing demand for the hair care products referred to as "hair relaxers," which can relax or straighten naturally curly or kinky hair. Hair relaxers may either be applied in a hair salon by a professional or in the home by the individual consumer.

Hair fibre, a keratinous material, comprises proteins (polypeptides). Many of the polypeptides in hair fibres are bonded together or cross-linked with disulfide bonds (—S—S—). A disulfide bond may be formed from the reaction of two sulfhydryl groups (—SH), one on each of two cysteine residues, which results in the formation of a cystine residue. A cystine residue comprises a cross-link of the formula —CH2-S—S—CH2- between 2 polypeptides.

While there are other types of bonds which occur between the polypeptides in hair fibres, such as ionic (salt) bonds, the permanent curling or the shape of the hair is essentially dependent on the disulfide bonds of cystine residues.

As a result, relaxing or straightening of hair can be achieved by disrupting the disulfide bonds of the hair fibres with an alkaline agent or a –2 reducing agent. The chemical disruption of disulfide bonds by an alkaline agent is usually combined with mechanical straightening of the hair, such as combing, and straightening generally occurs due to changes of the relative positions of opposite polypeptide chains within the hair fibre. The reaction is generally terminated by rinsing and/or the application of a neutralizing composition. The reaction with the alkaline agent is normally initiated by hydroxide ions.

Specifically, hydroxide ions initiate a reaction in which a cystine cross-link (—CH2-S—S—CH2-) is broken and a lanthionine cross-link (—CH2-S—CH2-) is formed.

Consequently, the term "lanthionizing" is used when one skilled in the art refers to the relaxing or straightening of keratin fibres by hydroxide ions.

Hair that has been lanthionized using hydroxide ion generating compositions frequently feels harsh and can break during grooming.

Thus, there is still a need for compositions and methods to relax keratin fibres which preserve the relaxing efficiency of hydroxide ion yet do not cause the negative attributes associated with lanthionized hair.

DESCRIPTION OF THE INVENTION

The present invention, in one aspect, provides an aqueous based hair straightening composition having a pH from 12 to 14 comprising
  i) an hydroxide ion generator; and
  ii) from 0.5 wt % to 20 wt % of the total composition of urea in which the weight ratio of urea to hydroxide generator is greater than 1:1.

In another aspect of the invention, there is provided a method for straightening hair comprising applying to the hair a composition described above.

A further aspect of this invention is the use of the urea in a hydroxide based straightening system to enhance the straightening activity and/or to mitigate hair damage.

DETAILED DESCRIPTION OF THE INVENTION

The straightening composition comprises urea.

The level of the urea compound ranges from 0.5 wt % to 20 wt % of the total composition, more preferably from 1 wt % to 15 wt %, most preferably from 3 to 10 wt %.

Any suitable hydroxide generator may be used in the composition, preferred are lithium hydroxide, potassium hydroxide and guanidine hydroxide. Sodium hydroxide is particularly preferred. In some cases, such as with guanidine hydroxide, it is preferred if the hydroxide is preferred in situ.

The hydroxide generator is preferably present at levels ranging from 0.1 wt % to 8 wt % of the total composition, more preferably from 0.5 wt % to 3 wt %.

It is preferred if the weight ratio urea hydroxide generator is from 20:1 to 2:1, more preferably from 12:1 to 3:1.

Other Constituents

It is preferred if the composition is in an aqueous base. Particularly preferred are base compositions comprising an oil-in-water emulsion.

Other constituents which can be used in the compositions of the invention can be chosen from solvents such as alcohol and water; preservatives; perfumes; UV filters; active hair care agents; plasticizers; anionic, cationic, amphoteric, non-ionic, and zwitterionic surfactants; hair conditioning agents such as silicone fluids, fatty esters, fatty alcohol, fatty chain hydrocarbons, emollients, lubricants, and penetrants such as lanolin compounds, protein hydrolysates, and other protein derivatives; anionic, cationic, amphoteric, nonionic, and zwitterionic polymers; dyes; tints; bleaches; reducing agents; pH adjusting agents; sunscreens; and thickening agents.

Products of the invention may further comprise organic nucleophiles chosen from basic amino acids such as lysine, amines, alcohols, and mercaptans and derivatives thereof. Ionic form (such as lysine) and/or in the form of derivatives thereof, e.g., an ammonium form (such as lysine hydrochloride) and/or a carboxylate form (such as sodium lysinate).

The preferred product form is a cream.

In one aspect the product is in the form of a kit consisting of two parts. The first part comprises the hydroxide components and is preferably formulated as a cream. The second part comprises the urea/urea based additive and may be in a liquid or solid form. The urea/urea based additive could be used either as neat active or as a diluted slurry, dispersion or solution. The two parts of the kit are mixed immediately before application to the hair. In the context of this invention the term "immediately before application" means approximately 5 minutes or less before application.

The invention will now be illustrated by the following non-limiting Examples. Examples of the invention are illustrated by a number, comparative examples are illustrated by a letter.

Relaxer Formulation with 2% Hydroxide

| Ingredient | Tradename | Supplier | Example A wt/% |
|---|---|---|---|
| Pet Jelly | Perfecta | Crompton | 15 |
| Mineral Oil 65/75 | 65/75 Grade | ex GTC | 20 |
| Cetearyl Alcohol & PEG-20 Stearate | Polawax GP200* | Croda | 3 |

-continued

| Ingredient | Tradename | Supplier | Example A wt/% |
|---|---|---|---|
| Cetearyl Alcohol | Laurex CS | Hunstman | 4 |
| EDTA Sodium | | Sigma-Aldrich | 0.1 |
| Polysorbate 60 | Tween 60 | Uniqema | 2 |
| PEG-75 Lanolin | Solan E Pellets | Croda | 0.625 |
| Propylene Glycol | | Sigma-Aldrich | 5 |
| NaOH | | Sigma-Aldrich | 2 |
| Water | | | to 100 wt % |

*Polawax GP200 is a mixture of PEG-20 Stearate and Cetearyl alcohol in a 1 to 4 ratio.

TABLE 2

| Ingredient | Ex 1 | Ex 2 | Ex 3 | Ex B |
|---|---|---|---|---|
| Pet Jelly | 15 | 15 | 15 | 15 |
| Mineral Oil | 20 | 20 | 20 | 20 |
| Polawax GP200 | 3 | 3 | 3 | 3 |
| Laurex CS | 4 | 4 | 4 | 4 |
| EDTA Sodium | 0.1 | 0.1 | 0.1 | 0.1 |
| Tween 60 | 2 | 2 | 2 | 2 |
| Solan E Pellets | 0.625 | 0.625 | 0.625 | 0.625 |
| Propylene Glycol | 5 | 5 | 5 | 5 |
| NaOH | 1.5 | 1.5 | 1.5 | 1.5 |
| Urea | 8 | 5 | 10 | 0 |
| Water | to 100 | to 100 | to 100 | to 100 |

A set of switches were treated with the relaxer cream containing 2% sodium hydroxide (Example A) a second set of switches were treated with 1.5% sodium hydroxide and 8% urea. The switches were treated consecutively for a total of 4 applications. Each cycle consisted of treatment with the relaxer cream for 20-30 minutes, rinsing, shampooing, rinsing, and blot drying. After the fourth application the switches were allowed to dry overnight (18 hrs) in controlled conditions 25° C. 50% RH.

The weight of the switches was recorded. The switches were mounted in an automatic combing device and subjected to a total of 6 hours dry combing, the weight of each switch was recorded after each hour.

The % breakage is calculated as the weight at a given time/initial weight×100.

| Combing times | % Breakage | |
|---|---|---|
| hours | Example A | Example 1 |
| 0 | 0 | 0 |
| 1 | 1.25 | 0.75 |
| 2 | 2.5 | 1.0 |
| 3 | 3.0 | 1.75 |
| 4 | 4.0 | 2.0 |
| 5 | 5.0 | 2.5 |
| 6 | 6.0 | 2.75 |

The straightening data was assessed by the mean absolute curvature ($mm^{-1}$) of the hair. The greater the curvature the curlier the hair.

| Example | Mean Absolute curvature $mm^{-1}$ |
|---|---|
| Water | 0.74 |
| A | 0.16 |
| B | 0.56 |
| 2 | 0.39 |
| 3 | 0.22 |
| 1 | 0.21 |

It is thus demonstrated that urea increases the effectiveness of a hydroxide based relaxing system while mitigating the damage caused by the hydroxide.

The invention claimed is:

1. An aqueous based hair straightening composition having a pH from 12 to 14 comprising, as a mixture prior to application to hair:
   i) a hydroxide based straightening system comprising a hydroxide ion generator selected from the croup consisting of lithium hydroxide, potassium hydroxide, guanidine hydroxide, sodium hydroxide and mixtures thereof; and
   ii) from 0.5 wt % to 20 wt % of the total composition of urea in which the weight ratio of urea to hydroxide generator is from 12:1 to 3:1 wherein components (i) and (ii) are applied as a mix comprising components i) and ii) before application to the hair and such mixture is applied within 5 minutes or less of mixing.

2. A hair straightening composition according to claim 1 in which the levels of compound ii) range from 1 wt % to 15 wt % of the total composition.

3. A hair straightening composition according to claim 1 in which the levels of hydroxide ion generator range from 0.5 wt % to 3 wt % of the total composition.

4. A method for lanthionizing keratin fibres to achieve relaxation of said keratin fibres in which a composition according to claim 1 is applied to the hair.

* * * * *